US005086171A

United States Patent [19]
Mathiaparanam

[11] Patent Number: 5,086,171
[45] Date of Patent: Feb. 4, 1992

[54] BIS-(INDOLYL)ETHYLENES

[75] Inventor: Ponnampalam Mathiaparanam, Appleton, Wis.

[73] Assignee: Appleton Papers Inc., Appleton, Wis.

[21] Appl. No.: 615,730

[22] Filed: Nov. 19, 1990

Related U.S. Application Data

[63] Continuation-in-part of Ser. No. 320,642, Mar. 8, 1987, Pat. No. 4,996,328.

[51] Int. Cl.[5] .......... C07D 413/00

[52] U.S. Cl. .......... 544/144; 544/142; 544/143; 546/200; 546/201; 548/452; 548/454; 548/455

[58] Field of Search .......... 548/455, 452, 454; 544/142, 143, 144; 546/200, 201

[56] References Cited

PUBLICATIONS

Chemical Abstracts-vol. 112:22353(a), "Bis(3-Indolyl-)Ethylene Dye Intermediates".

*Primary Examiner*—Marianne Cintins
*Assistant Examiner*—Jessica H. Nguyen
*Attorney, Agent, or Firm*—Benjamin Mieliulis

[57] ABSTRACT

Bis-(indolyl)ethylenes of the following general formula are prepared:

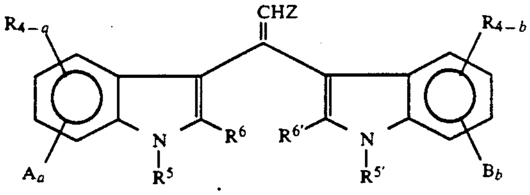

wherein a is 1 or 2, wherein b is 1 or 2, wherein each A is independently selected from a dialkylamino, dialkoxyalkylamino, diaroxyalkylamino, diarylamino, alkylarylamino, dicyloalkylamino, alkylcycloalkylamino, arylcycloalkylamino, pyrrolidino, piperidino, or morpholino radical, wherein each B is independently selected from A or an alkoxy, alkoxyalkyl or aroxy radical, wherein each R is independently selected from hydrogen, halogen, alkyl, or alkoxy, wherein each of $R^5$, $R^{5'}$, $R^6$, and $R^{6'}$ are each independently selected from hydrogen, alkyl ($C_1$-$C_8$), alkoxyalkyl, aroxyalkyl, halogen, phenyl, or phenyl substituted by alkyl or alkoxy, the alkyl moieties referred to herein being of one to eight carbons, the cycloalkyl moieties referred to herein being of three to six carbons.

10 Claims, 2 Drawing Sheets

BIS-(INDOLYL)ETHYLENES

This application is a continuation-in-part of Ser. No. 320,642 filed Mar. 8, 1989, now U.S. Pat. No. 4,996,328.

FIELD OF INVENTION

1. Background of Invention

This invention relates to bis-(indolyl)ethylenes and methods for their production. More particularly, this invention relates to chromogenic compounds which can give intense colors, when reacted with an electron accepting coreactant material. More specifically, this invention relates to methods for the production of such chromogenic compounds and novel pressure-sensitive or heat-sensitive mark-forming record systems incorporating such compounds. As used in mark-forming systems, marking in desired areas on support webs or sheets may be accomplished by effecting selective localized reactive contact between the chromogenic material and the electron-accepting material on or in such web or sheet, such material being brought thereto by transfer or originally there in situ. The selective reactive contact forms colored images in the intended image marking areas.

2. Description of Related Art

Several divinyl phthalide chromogenic compounds (C1) [(C) $L^1,L^2$=substituted phenyl] (read as Compound C1 arrived at by referring to formula C wherein $L^1$ and $L^2$ are as stated) have been prepared by the condensation of ethylenes (A1) [(A) $L^1,L^2$=substituted phenyl] with phthalic anhydrides (B1) [(B) Each Halogen is independently Cl or Br] in acetic anhydride (Sheldon Farber, U.S. Pat. Nos. 4,020,056, 4,022,771, 4,107,428, 4,119,776;)

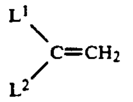

(A)

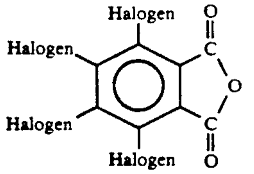

(B)

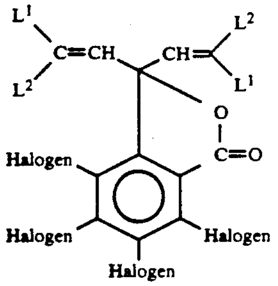

(C)

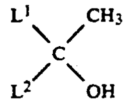

(D)

-continued

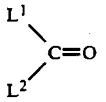

(E)

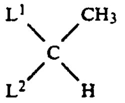

(F)

Substituted ethylenes (A1) or their precursors (D1) [(D) $L^1,L^2$=substituted phenyl] were prepared by the reaction of methylmagnesium bromide (also known as methyl Grignard reagent) with ketones (E1) [(E) $L^1,L^2$=substituted phenyl]. The use of a Grignard reaction to prepare (A1) imposes severe restrictions on the scaleup synthesis of (A1) and consequently on the manufacture of divinyl phthalides (C1).

In another synthetic approach, the alcohol (D1) was obtained by reacting the ethane (F1) [(F) $L^1,L^2$=substituted phenyl] with lead peroxide in either nitric acid or formic acid; and the substituted ethylene (A) was obtained from (D1) by dehydration [Yamada Kagaku, Japan Kokai 1988-8360, filed June 30, 1986].

When indole was heated with acetic anhydride containing 10% acetic acid a bis-(indolyl)ethylene (A2) [(A) $L^1,L^2$=1-acetylindole-3-yl] apparently Was obtained as a by-product in 5–10% yield (J. E. Saxton, J. Chem. Soc., 3592 (1952)].

Substituted (2- and 1,2-) indoles when reacted with acetyl cyanide in the presence of hydrogen chloride yielded 1-cyano-1,1-di(indole-3-ye)ethanes (G) and apparently some of these products may be converted to bis-(indolyl)ethylenes (H) by heating them under vacuum either alone or with soda lime. In some cases, dependent on certain select substituents M and W, (G) may yield some (H) type compounds on refluxing with aqueous-ethanolic 10% potassium hydroxide [A. K. Kiang and F. G. Mann, J. Chem., Soc., 594 (1953)].

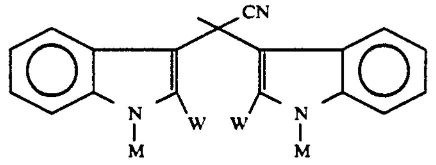

(G)

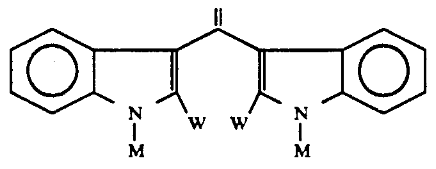

(H)

M = H, Ph
W = Me, Ph

Bis-(indolyl)ethylene (H1) [(H) M=H and W=Me] was speculated to be a product (m.p. 203° C.) from the reaction of 2-methylindole with ethyl acetate and sodium ethoxide. No other data were given to substantiate the structure [A. Angeli and G. Marchetti, Atti. Accad. Lincei, 16 (II), 179 (1907)].

In another report (W. Borsche and H. Groth, Annalen, 549, 238 (1941)], 2-methylindole when boiled with acetyl chloride formed a product that on treatment with alkali gave a pseudobase, ($C_{20}H_{18}N_2$, pale rose, m.p. 208° C.). The pseudobase was suggested to be 1-(2-methylindole-3-yl)-1-(2-methyl-3-indolidene)ethane (H2). Again, insufficient data precludes the substantiation of this structure. Furthermore, similar structure was proposed for the pseudobase obtained by substituting 2-phenylindole for 2-methylindole.

(H2)

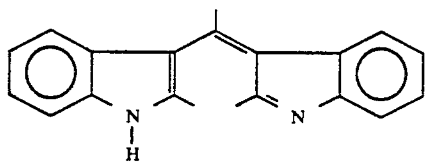

U.S. Pat. Nos. 4,897,494 and 4,931,567 disclose several symmetrical bis-(indolyl)ethylene compounds. Unsymmetrical types of bis-(indolyl)ethylenes are not taught or suggested.

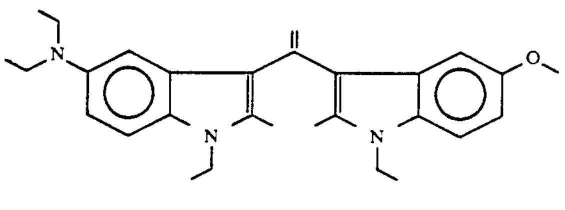

1-(5-diethylamino-1-ethyl-2-methylindole-3-yl)-1-(1-ethyl-5-methoxy-2-methylindole-3-yl)ethylene.

Figure 1:
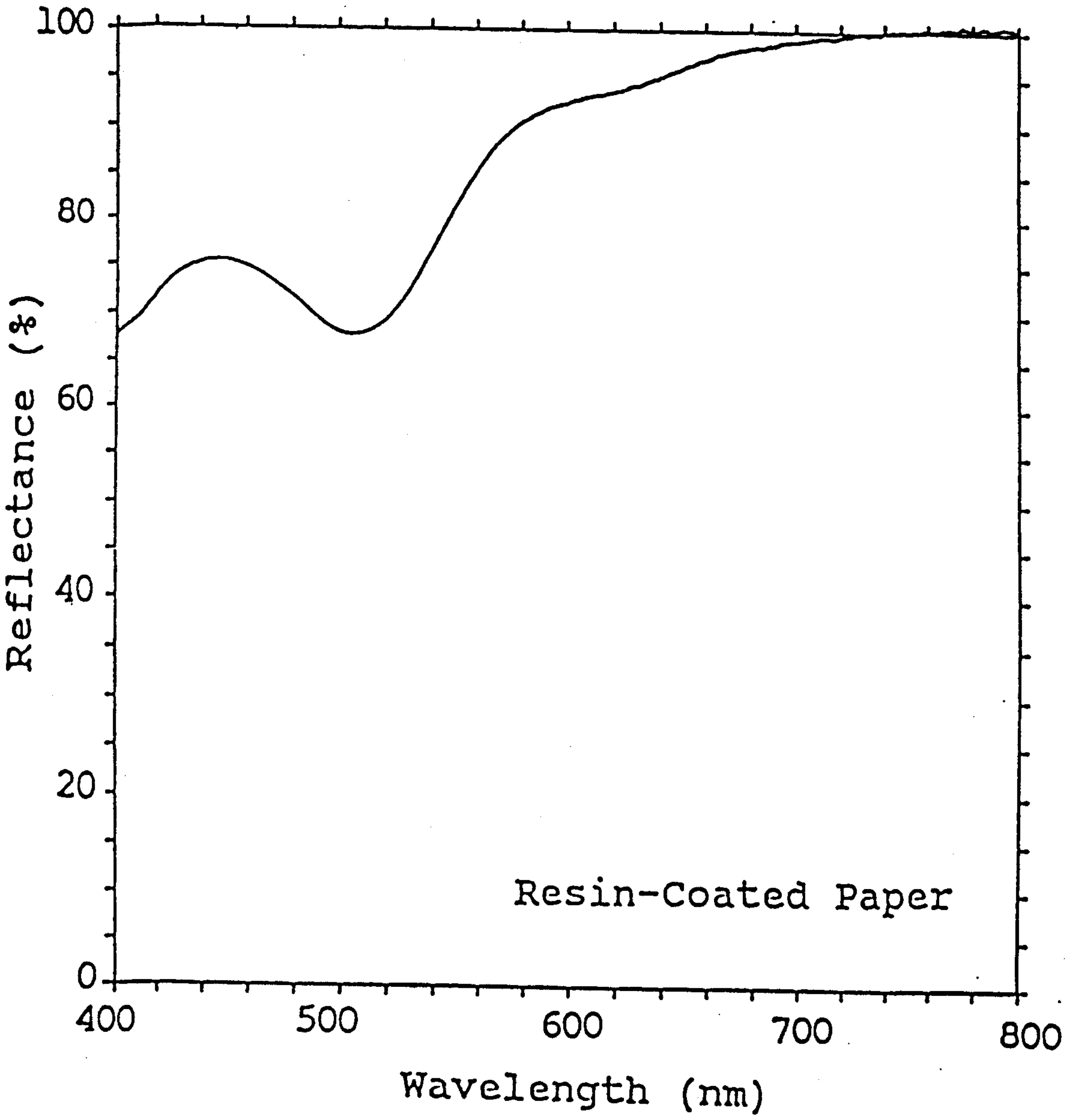
FIG. 1 is a graph of reflectance (%) from 400 to 800 nm for the following compound on resin-coated paper.
Figure 2:
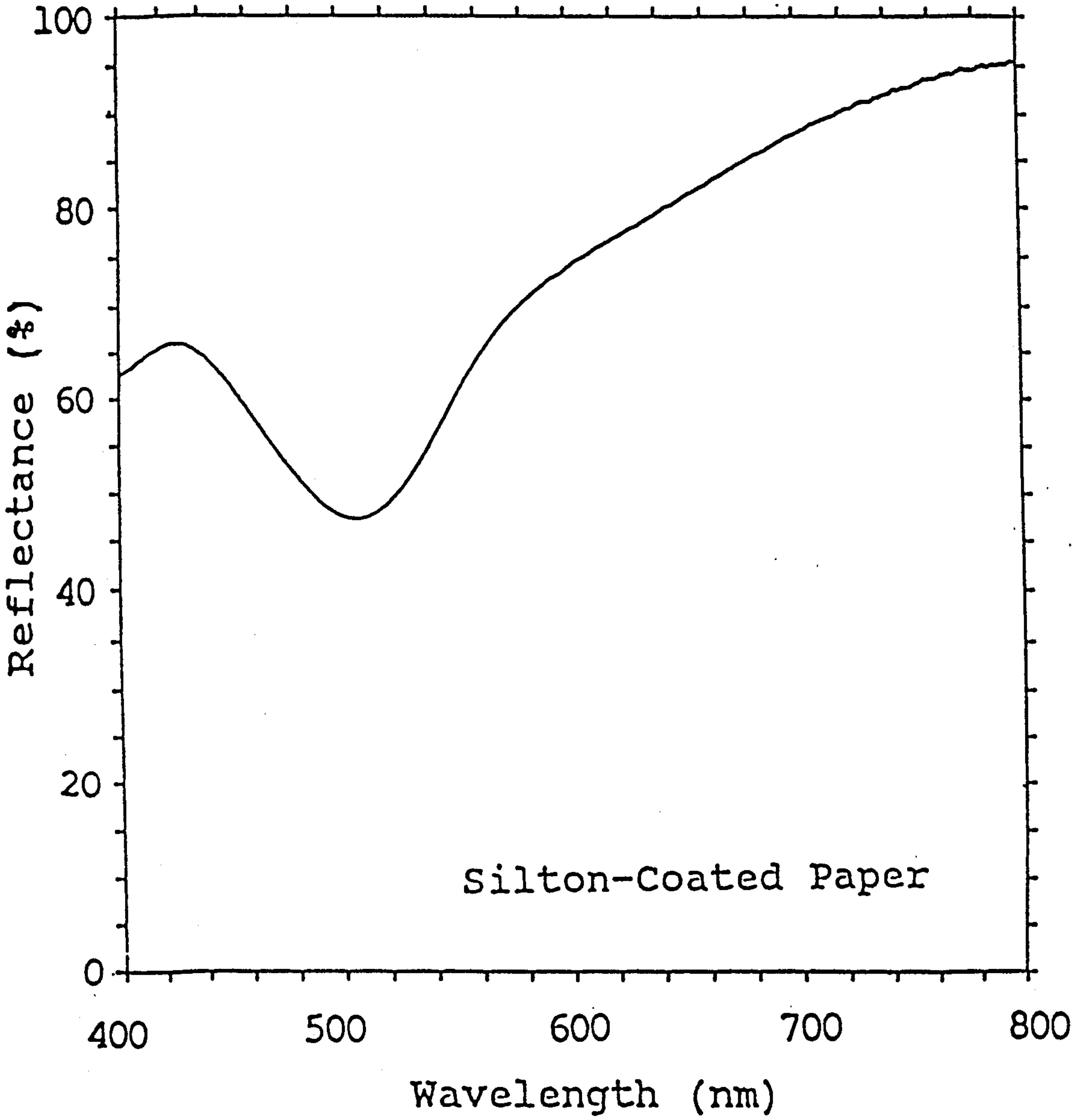

FIG. 2 is a graph of reflectance of the above compound when applied on silton-coated paper. Example 3 details the synthesis of this specific compound.

DETAILED DESCRIPTION OF THE INVENTION

A novel method for producing bis-(indolyl)ethylenes and novel bis-(indolyl)ethylene compounds are described along with record systems incorporating such compounds.

In the process of the invention bis-(indolyl)ethylenes of the following formula are prepared:

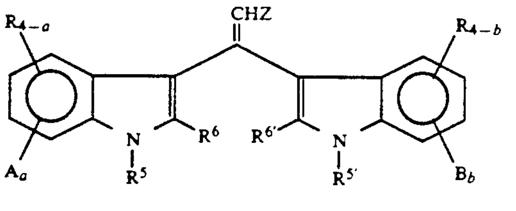

(1)

wherein a is 1 or 2, wherein b is 1 or 2, wherein each A is independently selected from a dialkylamino, dialkoxyalkylamino,diaroxyalkylamino, diarylamino, alkylarylamino, dicycloalkylamino, alkylcycloalkylamino, arylcycloalkylamino, pyrrolidino, piperidino, or morpholino radical, wherein each B is independently selected from A or an alkoxy, alkoxyalkyl or aroxy radical, wherein each R is selected from hydrogen, halogen, alkyl or alkoxy, wherein each of $R^5$, $R^{5'}$, $R^6$ and $R^{6'}$ are each independently selected from hydrogen, alkyl($C_1$-$C_8$), alkoxyalkyl, aroxyalkyl, cycloalkyl ($C_3$-$C_6$), phenyl, and phenyl substituted by alkyl($C_1$-$C_8$) or alkoxy ($C_1$-$C_8$), wherein Z is selected from hydrogen, alkyl($C_1$-$C_8$), alkoxyalkyl, aroxyalkyl, halogen, phenyl or phenyl substituted by alkyl or alkoxy, the alkyl moieties referred to herein being of one to eight carbons, the cycloalkyl moieties referred to herein being of three to six carbons.

With pyrrolidino, piperidino or morpholino radicals, the following are preferable.

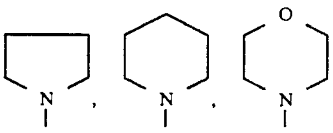

Bonding through locations other than the nitrogen can be accomplished, but the yields are reduced to the extent to make them unattractive.

The bis(indolyl)ethylenes of the invention are formed by three major routes. The first route comprises condensing the corresponding indoles, in acid anhydride (such as $(ZCH_2CO)_2O$, Z as defined elsewhere) and Lewis Acid such as zinc chloride or other electron acceptor preferably in approximately 1:1:0.5 molar ratios respectively in a suitable solvent. The second route comprises condensing corresponding indoles with acid chloride (such as $ZCH_2COCl$, Z as defined earlier) preferably in approximately 1:(0.15-2.0) molar amounts at temperatures (15°-75° C.) with or without solvent. The third route involves a condensation of a substituted or unsubstituted indole (See "Synthesis Routes", Process III herein) with a acyl indole of the type

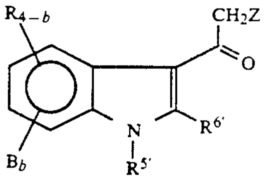

in the presence of a Vilsmeier reagent (such as dialkyl chlorophosphates, phosphoryl chloride, phosgene, oxalyl chloride, benzoyl chloride, alkanesulfonyl chloride, arenesulfonyl chloride, alkyl chloroformate and aryl chloroformate) with or without solvent. Lewis acid (such as zinc chloride) can be used in conjunction with these Vilsmeier reagents to increase yield. Significantly, the third route recited is particularly useful for preparing unsymmetrical indolyl ethylenes having at least one amino substituent on the phenyl ring.

A in formula 1 type compounds is preferred when it is of the dialkylamino, dialkoxyalkylamino, alkylarylamino, dicycloalkylamino, alkylcycloalkylamino, or arylcycloalkylamino type of radical. More particularly, this class of bis(indolyl)ethylenes can be described by the following formula.

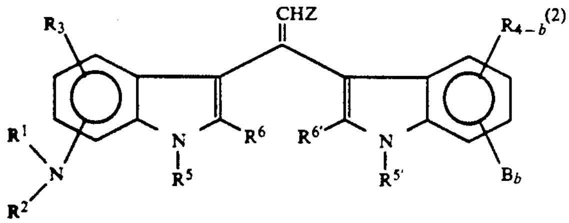
(2)
wherein $R^1$ and $R^2$ are each independently selected from alkyl ($C_1$-$C_8$), alkoxyalkyl, aroxyalkyl, cycloalkyl ($C_3$-$C_6$), phenyl, phenyl substituted by alkyl ($C_1$-$C_8$) or alkoxy ($C_1$-$C_8$),
wherein c is an integer from 1 to 3
wherein R, B, b, $R^5$, $R^{5'}$, $R^6$, $R^{6'}$, and Z are as previously defined herein.
Illustrative compounds of the invention include:
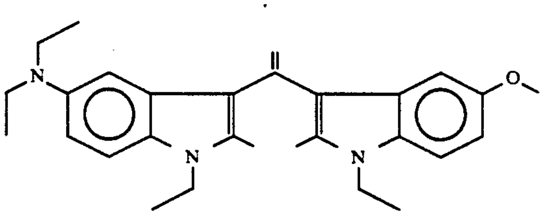
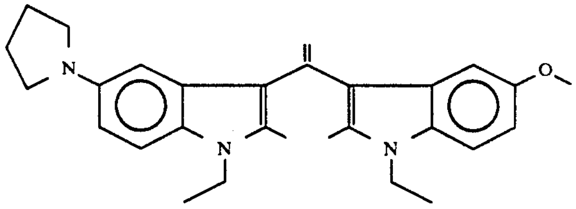
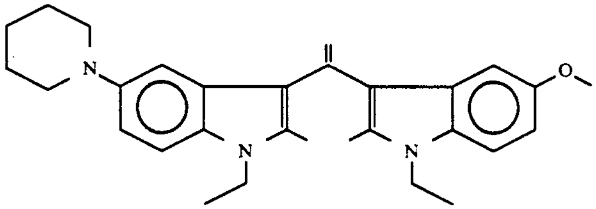
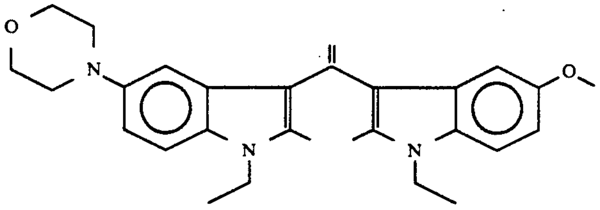
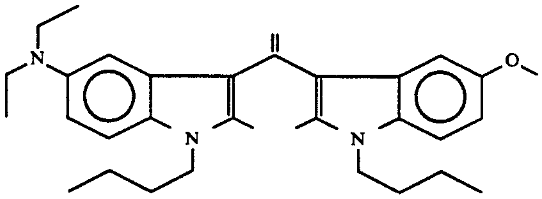
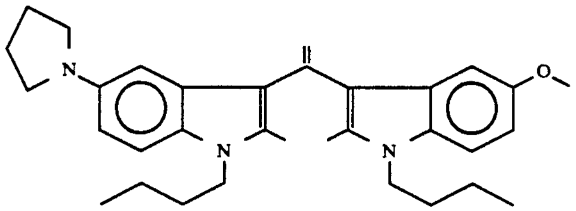

-continued
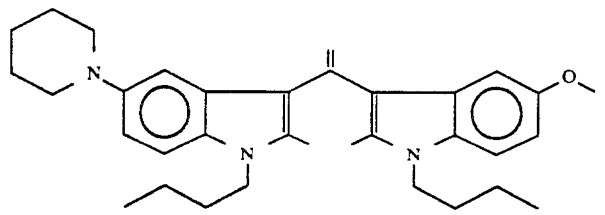
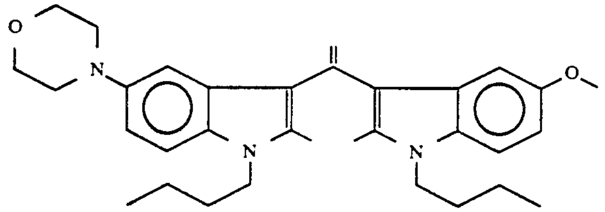
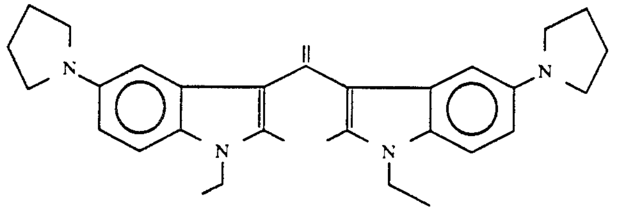
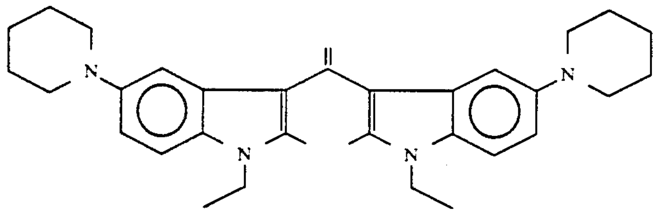
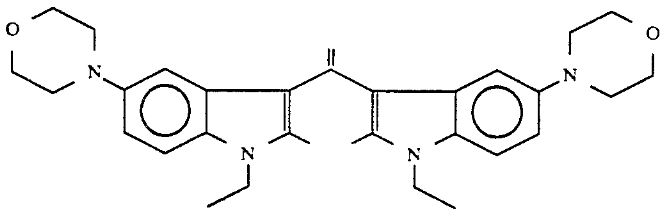
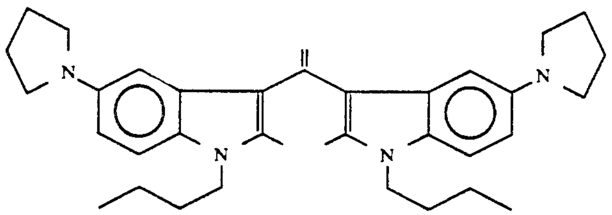
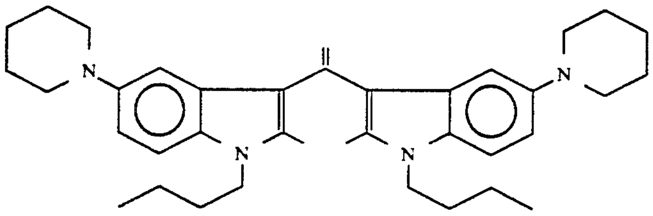

-continued

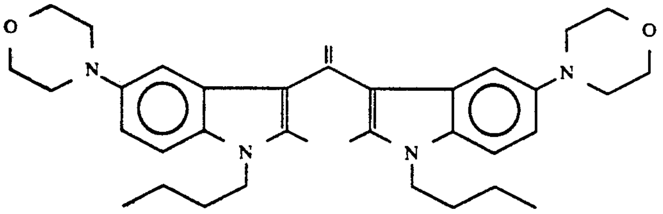

The chromogenic compounds of the invention of color form have absorbance at approximately 400–700 nm and thus are eligible for use in pressure-sensitive and thermal recording systems. Compounds which are chromogenic and absorptive in the visible region of the spectrum have commercial utility by being capable, when imaged, of being detected by optical reading machines.

The colorable chromogenic compounds are eligible for use in pressure-sensitive recording and thermal recording systems. Advantageously recording systems utilizing these compounds can be read by optical reading machines, particularly those capable of reading for the wavelength range of 400–700 nm.

Table 1 presents the reflectance and color of certain indolyl (ethylenes) on resin coated and silton-coated papers.

TABLE 1

REFLECTANCE MINIMA AND COLOR OF (INDOYL) ETHYLENES ON RESIN-COATED AND SILTON-COATED PAPERS.

| ENTRY | COMPOUND | REFLECTANCE MINIMA (nm) AND COLOR ON RESIN-COATED | SILTON-COATED |
|---|---|---|---|
| 1 | 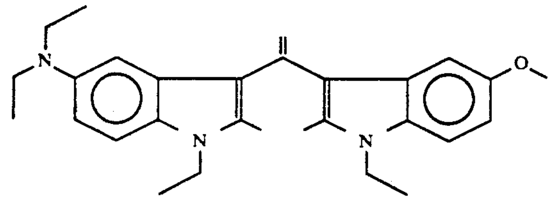 | 507 Light Pink | 507 Pink |
| 2 | 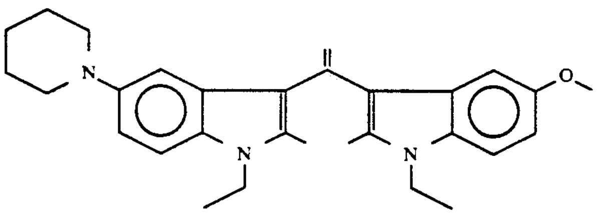 | 514 Light Pink | 508 Pink |
| 3 | 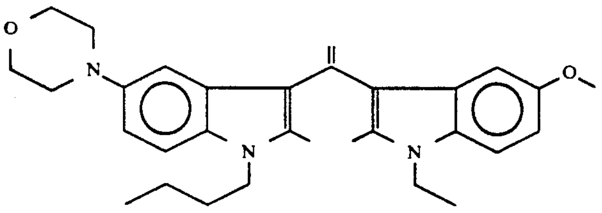 | 521 Pink | 517 Purple |
| 4 | 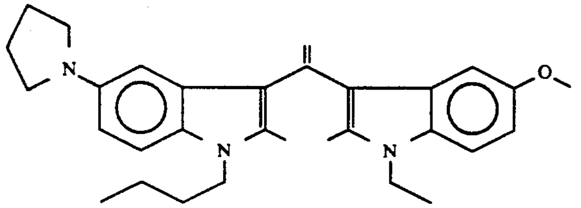 | 504 Purple | 500 Purple |

The colorable chromogenic compounds of the invention, can be combined with other chromogenic materials covering other or wider spectral ranges and can be used in pressure-sensitive and thermal recording systems to provide images which absorb over wider ranges of the electromagnetic spectrum. The commercial significance is that a larger assortment of available optical readers can thus be effectively useful with such imaged record systems.

The chromogenic compounds of the invention also find use in photosensitive printing material, typewriter ribbons, inks and the like.

According to the first process of the invention, the bis-(indolyl)ethylenes, are prepared by condensing an indole, which can be substituted with any of one or more of $R^5$, $R^6$, A or B, with acid anhydride $[(ZCH_2CO)_2O]$ in the presence of an electron acceptor or acidic type compounds belonging to:

Carboxylic Acids (e.g. Acetic Acid); or
Sulfonic Acids (e.g. p-Toluenesulfonic Acid); or
Acid Chlorides (e.g. Benzoyl Chloride); or
Lewis Acids (e.g. Zinc Chloride, Boron Trifluoride)

and the like, in solvents, preferably organic, or more preferably the halogenated organic solvents such as 1,2-dichloroethane and chlorobenzene and the like. The acidic compounds listed above are illustrative rather than comprehensive as they are well known in the art.

For example, an indole substituted optionally with any of one or more of $R^5$, $R^6$, A or B, can be refluxed with zinc chloride and acetic anhydride in 1,2-dichloroethane. After about one hour, the starting material disappears and the reaction mixture contains the bis-(indolyl)ethylene as the major product. The yield appears to depend on the relative molar amounts of indole, acetic anhydride and zinc chloride, and preferred appears to be a molar ratio of 1:1:0.5 of the preceding materials respectively.

Equimolar amounts of the indole and acetic anhydride are preferred for complete reaction, but half the molar amount of zinc chloride appears sufficient to carry out the reaction.

In the second process, bis-(indolyl)ethylenes are prepared by reacting the indoles with acid chloride ($ZCH_2COCl$) with or without solvent in the temperature range 15°-75° C.

Acetic anhydride appears to be the best solvent for the reaction and varying amounts of acetyl chloride (0.015-0.1 mole) can be used with variable reaction times (3-20 hours were used at 50°-52° C.). The reaction time appears inversely proportional to the acetyl chloride concentration.

In the third process for the production of bis-(indolyl-)ethylenes, acylindole is condensed with an indole using Vilsmeier reagents (such as dialkyl chlorophosphate, phosphoryl chloride, phosgene, oxalyl chloride, benzoyl chloride, alkane or arenesulfonylchloride and alkyl or arylchloroformate) with or without solvent. Lewis acid (such as zinc chloride) can be used in conjunction with the Vilsmeier reagent to increase yield. This process is very versatile because symmetrical as well as unsymmetrical bis-(indolyl)ethylenes can be produced. In all three processes the indole or acylindole can be optionally substituted by any of A, B, $R^5$, or $R^6$ as earlier defined. This condensation reaction can be carried out on using acylindole and indole together with phosphoryl chloride as a condensing agent in 1,2-dichloroethane as solvent. For example, a solution of acylindole in 1,2-dichloroethane can be cooled in an ice/salt bath and phosphoryl chloride was added slowly, keeping the temperature of the reaction mixture between 0° and 5° C. during the addition. This low temperature is preferable during the initial stages of reaction to minimize the formation of unwanted byproducts. After 30 minutes stirring while the reaction mixture is warmed to room temperature, the indole in 1,2-dichloroethane is added. The reaction mixture is stirred overnight at room temperature to effect reaction. The condensation reaction can be further driven to completion by refluxing the reaction mixture for one hour.

SYNTHESIS ROUTES:

Process I.

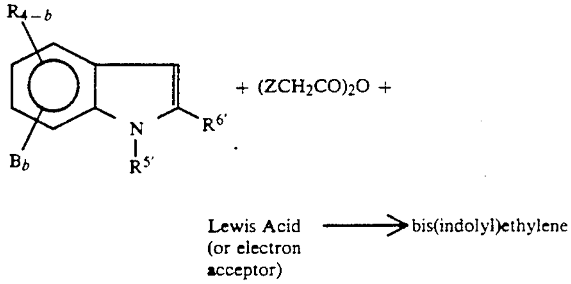

Process II.

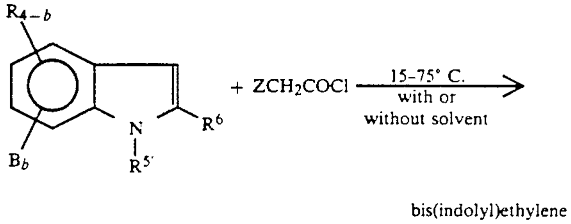

Process III.

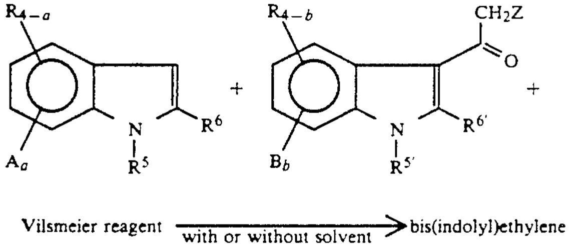

All of these processes discussed so far for the production of bis-(indolyl)ethylenes are very conducive to scale-up.

In forming pressure sensitive or heat sensitive mark forming record systems with the bis-(indolyl)ethylenes of the invention, the eligible acidic, or electron acceptor materials include, but are not limited to, acid clay substances such as attapulgite, bentonite and montmorillonite and treated clays such as silton clay as disclosed in U.S. Pat. Nos. 3,622,364 and 3,753,761, phenols and diphenols as disclosed in U.S. Pat. No. 3,539,375, aromatic carboxylic acids such as salicylic acid, metal salts of aromatic carboxylic acids as disclosed in U.S. Pat. No. 4,022,936 and acidic polymeric material such as phenol-formaldehyde polymers as disclosed in U.S. Pat. No. 3,672,935 and oil-soluble metal salts of phenol-formaldehyde polymers as disclosed in U.S. Pat. No. 3,732,120. The compounds of this invention are useful as color formers in recording materials such as, for example, pressure-sensitive copying paper, thermally-responsive record material, electro heat-sensitive recording paper and thermal ink.

Pressure-sensitive copying paper systems provide a marking system and can be assembled by disposing on and/or within sheet support material unreacted mark-forming components and a liquid solvent in which one or both of the mark-forming components is soluble, said liquid solvent being present in such form that it is maintained isolated by a pressure-rupturable barrier from at least one of the mark-forming components until application of pressure causes a breach of the barrier in the area delineated by the pressure pattern. The mark-forming components are thereby brought into reactive contact, producing a distinctive mark.

The pressure-rupturable barrier, which maintains the mark-forming components in isolation, preferably comprises microcapsules containing liquid solvent solution. The microencapsulation process utilized can be chosen from the many known in the art. Well known methods are disclosed in U.S. Pat. Nos. 2,800,457; 3,041,289; 3,533,958; 3,755,190; 4,001,140 and 4,100,103. Any of these and other methods are suitable for encapsulating the liquid solvent containing the chromogenic compounds of this invention.

The chromogenic compounds of this invention are particularly useful in pressure-sensitive copying paper systems which incorporate a marking liquid comprising a vehicle in which is dissolved a complement of several colorless chromogenic compounds each exhibiting its own distinctive color on reaction with an eligible acidic record material sensitizing substance. Such marking liquids are disclosed in U.S. Pat. No. 3,525,630.

Thermally-responsive record material systems provide a marking system of color-forming components which relies upon melting or subliming one or more of the components to achieve reactive, color-producing contact. The record material includes a substrate or support material which is generally in sheet form. The components of the color-forming system are in a substantially contiguous relationship, substantially homogeneously distributed throughout a coated layer material deposited on the substrate. In manufacturing the record material, a coating composition is prepared which includes a fine dispersion of the components of the color-forming system, polymeric binder material, surface active agents and other additives in an aqueous coating medium.

The chromogenic compounds of this invention are useful in thermally-responsive record material systems either as single chromogenic compounds or in mixtures with other chromogenic compounds. Examples of such systems are given in U.S. Pat. Nos. 3,539,375 and 4,181,771.

Thermally-responsive record material systems are well known in the art and are described in many patents, for example U.S. Pat. Nos. 3,539,375; 3,674,535; 3,746,675; 4,151,748; 4,181,771; and 4,246,318 which are hereby incorporated by reference. In these systems, basic chromogenic material and acidic color developer material are contained in a coating on a substrate which, when heated to a suitable temperature, melts or softens to permit said materials to react, thereby producing a colored mark.

In the field of thermally-responsive record material, thermal sensitivity (response) is defined as the temperature at which a thermally-responsive record material produces a colored image of satisfactory intensity (density). Background is defined as the amount of coloration of a thermally-responsive record material before imaging and/or in the unimaged areas of an imaged material. The ability to maintain the thermal sensitivity of a thermally-responsive record material while reducing the background coloration is a much sought after and very valuable feature.

One of the uses for thermally-responsive record material which is enjoying increasing importance is facsimile reproduction. Alternative terms for facsimile are telecopying and remote copying. In the facsimile system, images transmitted electronically are reproduced as hard copy. One of the important requirements for thermally-responsive record material to be used in facsimile equipment is that it have good (low coloration) background properties.

Increases in the sensitivity of thermally-responsive record material have been achieved through the incorporation of a phenylhydroxynaphthoate compound or a hydroxyanilide compound in the color-forming composition along with the chromogenic material and developer material as disclosed in U.S. Pat. No. 4,470,057 or U.S. Pat. No. 4,535,347, respectively, by Kenneth D. Glanz. Such sensitizer materials can be advantageously used in combination with the present invention.

The record material includes a substrate or support material which is generally in sheet form. For purposes of this invention, sheets also mean webs, ribbons, tapes, belts, films, cards and the like. Sheets denote articles having two large surface dimensions and a comparatively small thickness dimension. The substrate or support material can be opaque, transparent or translucent and could, itself, be colored or not. The material can be fibrous including, for example, paper and filamentous synthetic materials. It can be a film including, for example, cellophane and synthetic polymeric sheets cast, extruded, or otherwise formed. The gist of this invention resides in the color-forming composition coated on the substrate. The kind or type of substrate material is not critical.

Although not required to practice and demonstrate the beneficial properties of the claimed invention, the inclusion of certain sensitizing materials in the color-forming system provides a further improvement in properties, especially increases in sensitivity. Materials such as phenyl-1-hydroxy-2-naphthoate, stearamide, 1,2-diphenoxyethane and p-hydroxyoctadecananilide are useful as such sensitizing materials.

The components of the color-forming system are in a contiguous relationship, substantially homogeneously distributed throughout the color-forming system, preferably in the form of a coated layer deposited on the substrate. In manufacturing the record material, a coating composition is prepared which includes a fine dispersion of the components of the color-forming system, polymeric binder material, surface active agents and other additives in an aqueous coating medium. The composition can additionally contain inert pigments, such as clay, talc, aluminum hydroxide, calcined kaolin clay and calcium carbonate; synthetic pigments, such as urea-formaldehyde resin pigments; natural waxes such as carnauba wax; synthetic waxes; lubricants such as zinc stearate; wetting agents and defoamers.

The color-forming system components are substantially insoluble in the dispersion vehicle (preferably water) and are ground to an individual average particle size of between about 1 micron to 10 microns, preferably about 1 to 3 microns. The polymeric binder material is substantially vehicle soluble, although latexes are also eligible in some instances. Preferred water-soluble binders include polyvinyl alcohol, hydroxy ethylcellulose, methylcellulose, hydroxypropylmethylcellulose, starch, modified starches, gelatin and the like. Eligible latex materials include polyacrylates, polyvinylacetates, polystyrene, and the like. The polymeric binder is used to protect the coated materials from brushing and handling forces occasioned by storage and use of the thermal sheets. Binder should be present in an amount to afford such protection and in an amount less than will interfere with achieving reactive contact between color-forming reactive materials.

Coating weights can effectively be about 3 to about 9 grams per square meter (gsm) and preferably about 5 to about 6 gsm. The practical amount of color-forming materials is controlled by economic considerations, functional parameters and desired handling characteristics of the coated sheets.

EXAMPLES

In the following examples, general procedures for preparing certain bis(indolyl)ethylenes according to the invention are described; the examples are not intended to be exhaustive. Unless otherwise noted, all measurements, percentages and parts are by weight.

Satisfactory spectroscopic data were obtained for the new compounds synthesized.

EXAMPLE 1

Condensation of 5-diethylamino-1-ethyl-2-methylindole with 3-acetyl-1-ethyl-5-methoxy-2-methylindole using Phosphoryl chloride 5-Diethylamino-1-ethyl-2-methylindole(1.2 g, 5 mmoles), 3-acetyl-1-ethyl-5-methoxy-2-methylindole(1.4 g, 6 mmoles) and Phosphoryl chloride(0.8 g, 5.2 mmoles) in 1,2-dichloroethane(20 ml) was stirred at room temperature in a flask equipped with a magnetic stirrer and a reflux condenser carrying a drying tube. After two hours, the gas chromatographic analysis of the reaction mixture indicated no reaction, only the starting materials were present. Then, the reaction mixture the reaction mixture was refluxed overnight and monitored by gas chromatography. The reaction mixture contained a mixture of products: 5-diethylamino-1-ethyl-2-methylindole(one of the starting materials), 1-(5-diethylamino-1-ethyl-2-methylindole-3-yl)-1-(1-ethyl-5-methoxy-2-methylindole-3-yl)ethylene (expected product) and two other unidentified products.

EXAMPLE 2

Condensation of 5-diethylamino-1-ethyl-2-methylindole with 3-acetyl-1-ethyl-5-methoxy-2-methylindole using Phosphoryl chloride and zinc chloride 5-Diethylamino-1-ethyl-2-methylindole(230 mg, 1 mmole), 3-acetyl-1-ethyl-5-methoxy-2-methylindole(250 mg, 1.08 mmoles), Phosphoryl chloride(170 mg, 1.1 mmoles) and zinc chloride(150 mg, 1.1 mmoles) in 1,2-dichloroethane(5 ml) was stirred at room temperature in a flask equipped with a magnetic stirrer and a reflux condenser carrying a drying tube. After two hours, gas chromatographic analysis of the reaction mixture indicated no reaction. Then, the reaction mixture was refluxed overnight and monitored by gas chromatography. The reaction mixture contained 1-(5-diethylamino-1-ethyl-2-methylindole-3-yl)-1-(1-ethyl-5-methoxy-2-methylindole-3-yl)ethylene as the major product.

EXAMPLE 3

Preparation of 1-(5-diethylamino-1-ethyl-2-methylindole-3-yl)-1-(1-ethyl-5-methoxy-2-methylindole-3-yl)ethylene

[Table 1, Entry 1]

A mixture of 3-acetyl-1-ethyl-5-methoxy-2-methylindole(2.3 g, 0.01 mole), 5-diethylamino-1-ethyl-2-methylindole(2.3 g, 0.01 mole), zinc chloride(1.40 g, 0.01 mole) and Phosphoryl chloride(1.5 g, 0.01 mole) in 1,2-dichloroethane(20 ml) was stirred at room temperature in a flask equipped with a magnetic stirrer and a reflux condenser carrying a drying tube. Then, the reaction mixture was refluxed overnight. Aqueous sodium hydroxide(10%, 50 ml) was added and the reaction mixture was kept at 70° C. with stirring for 2 hours; organic layer separated, washed, dried and concentrated. The residue was purified by chromatography on silica gel using toluene and toluene:acetone::4:1 as eluents. The product, straw-colored syrup, was obtained in 85%(3.8 g) yield. Mass spectrum gave $M^+$ at m/e 443.

A solution of the product gives a light pink color to paper coated with a phenolic resin, with reflectance minimum at 507 nm; and a pink color to paper coated with silton clay with reflectance minimum at 507 nm.

EXAMPLE 4

Preparation of 1-(1-n-butyl-2-methyl-5-N-morpholinoindole-3-yl)-1-1-(1-ethyl-5-methoxy-2-methylindole-3-yl)ethylene

[Table 1, Entry 3]

3-Acetyl-1-ethyl-5-methoxy-2-methylindole(2.4 g, 0.01 mole), 1-n-butyl-2-methyl-5-N-morpholinoindole(2.7 g, 0.01 mole), zinc chloride(1.4 g, 0.01 mole) and Phosphoryl chloride(1.5 g, 0.01 mole) in 1,2-dichloroethane(50 ml) was stirred at room temperature for two hours with exclusion of moisture. Then, the reaction mixture was refluxed overnight, treated with aqueous sodium hydroxide (10%, 100 ml) and toluene(100 ml) and the reaction mixture was stirred at 80° C. for one hour. The organic layer was separated, washed with hot water, dried and concentrated under reduced pressure. The residue was purified by column chromatography on silica gel using toluene and toluene:acetone::4:1 as eluents. The product was obtained as a straw-colored syrup, yield: 4.62 g (95%). Mass spectrum gave $M^+$ at m/e 485.

A solution of the product gives a pink color to paper coated with a phenolic resin, with reflectance minimum at 521 nm; and a purple color to paper coated with silton clay, with reflectance minimum at 517 nm.

EXAMPLE 5

Example of Pressure-Sensitive Record Material

Formulations and techniques for the preparation of carbonless copy paper are well known in the art, for example, as disclosed in U.S. Pat. Nos. 3,627,581; 3,775,424; and 3,853,869 incorporated herein by reference. CF sheets used with the CB sheets to form a manifold assembly are well known in the art. Substrate sheets containing oil-soluble metal salts of phenol-formaldehyde novolak resins of the type disclosed in U.S. Pat. Nos. 3,675,935; 3,732,120; and 3,737,410 are exemplary thereof. A typical example of a suitable acidic resin is a zinc modified, oil-soluble phenol-formaldehyde resin such as the zinc salt of a para-octylphenolformaldehyde resin or the zinc salt of a para-phenyl-phenol-formaldehyde resin.

| Color former solution: | Parts |
|---|---|
| bis indolylethylene | 5.6 |
| ex. 1-(1-n-butyl-2-methyl-5-N-morpholinoindole-3-yl)-1-(1-ethyl-5-methoxy-2-methylindole-3-yl)ethylene | |
| C10-C15 alkylbenzene | 130.0 |
| ex. Alkylate 215 | |
| (ethylphenyl)phenylmethane | 70.0 |

The color former solution is emulsified into a mixture of 35 parts of 10% EMA 31 [ethylene-maleic anhydride copolymer with a molecular weight range of 75,000 to 90,000 (Monsanto)] in water, 32 parts of 20% EMA 1103 [ethylene maleic anhydride copolymer with a molecular weight range of 5,000 to 7,000 (Monsanto)] in water, 133 parts water, 10 parts urea, and 1 part resorcinol, adjusted to pH 3.5. Following emulsification 29 parts of 37% formaldehyde is added and the mixture placed in a 55° C. water bath with stirring. After two hours, with stirring maintained, the temperature of the water bath is allowed to equilibrate with ambient temperature. The capsules are used to prepare a paper coating slurry.

| | Parts Wet | Parts Dry |
|---|---|---|
| capsule slurry | 80 | 40 |
| wheat starch granules | 10 | 10 |
| etherified corn starch binder | 40 | 4 |
| ex. Penford 230, 10% | | |
| (Penwick and Ford Ltd.) | | |
| water | 100 | — |

The slurries are applied to a paper base and drawn down with a No. 12 wire wound coating rod and the coatings dried. The resulting CB coatings are coupled with a sheet comprising a zinc-modified phenolic resin as disclosed in U.S. Pat. Nos. 3,732,120 and 3,737,410. Upon pressure contact, a visible image forms corresponding to the localized contact. Color formers can be versatilely mixed for color customization.

EXAMPLE 6

Example of Heat-Sensitive Record Material

The coating is prepared by milling the components in an aqueous solution of the binder until a particle size of between 1 and 10 microns is achieved. The milling is accomplished in an attritor, small media mill, or other suitable dispensing vehicle. The desired average particle size is 1 to 3 microns.

Separate dispersions of chromogenic compound, acidic developer material, and sensitizer are prepared.

| | Parts |
|---|---|
| Chromogenic Dispersion A | |
| bis-indolylethylene | 39.10 |
| ex. 1-(1-n-butyl-2-methyl-5-N-morpholinoindole-3-yl)-1-(1-ethyl-5-methoxy-2-methylindole-3-yl)ethylene | |
| binder, 20% polyvinylalcohol in water | 28.12 |
| water | 45.00 |
| defoamer and dispersing agent | 00.28 |
| ex Nopko NDW (sulfonated castor oil of Nopko Chemical Co.) | |
| Surfynol 104 | 10.60 |
| (a di-tertiary acetylene glycol surface active agent) | |
| Acidic Developer Material Dispersion B | |
| acidic developer material | 13.60 |
| ex. 4,4'-isopropylidenediphenol | |
| binder, 10% polyvinylalcohol in water | 24.00 |
| water | 42.35 |
| defoamer, Nopko NDW | 00.05 |
| Surfynol | 00.60 |
| Sensitizer Dispersion C (optional) | |
| sensitizer | 13.60 |
| ex. phenyl-1-hydroxy-2-naphthoate or 1,2-diphenoxyethane U.S. Pat. No. 4,531,140 | |
| binder, 10% polyvinylalcohol in water | 24.00 |
| water | 42.35 |
| defoamer, Nopko NDW | 00.05 |
| Surfynol | 00.60 |

The above separate dispersions, A, B, and C, can be combined as follows, and optionally include zinc stearate, 21% dispersion, urea formaldehyde resin, and micronized silica.

The above dispersions are combined 0.6 parts A, 4.9 parts B, 3.3 parts C, along with 1.4 parts zinc stearate dispersion, 4.3 parts water, 1.9 parts polyvinylalcohol and 0.6 parts urea formaldehyde resin. This mix is applied to paper and dried yielding a dry coat weight of 5.2 to 5.9 gsm. The resultant paper is sensitive to applied heat such as via a thermal print head.

What is claimed is:

1. Chromogenic bis-(indolyl)ethylene of the formula

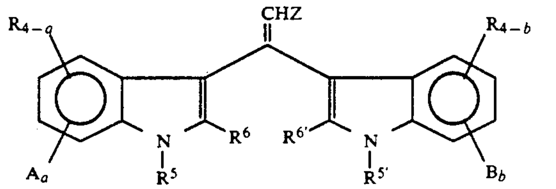

wherein a is 1 or 2, wherein b is 1 or 2, wherein each A is selected from the group consisting of a dialkylamino, dialkoxyalkylamino,diaroxyalkylamino,diarylam alkylarylamino, dicycloalkylamino, alkylcycloalkylamino, arylcycloalkylamino, pyrrolidino, piperidino, and morpholino radical, wherein each B is selected from the group consisting of A, alkoxy, alkoxyalkyl and aroxy radical, wherein each R is selected from the group consisting of hydrogen, halogen, alkyl, and alkoxy, wherein each of $R^5$, $R^{5'}$, $R^6$, $R^{6'}$ are selected from the group consisting of hydrogen, alkyl ($C_1$-$C_8$), alkoxyalkyl, aroxyalkyl, cycloalkyl ($C_3$-$C_6$), phenyl, and phenyl substituted by alkyl ($C_1$-$C_8$) or alkoxy ($C_1$-$C_8$), wherein Z is selected from the group consisting of hydrogen, alkyl ($C_1$-$C_8$), alkoxyalkyl, aroxyalkyl, halogen, phenyl, and phenyl substituted by alkyl or alkoxy, the alkyl moieties referred to herein being of one to eight carbons, the cycloalkyl moieties referred to herein being of three to six carbons.

2. A bis-(indolyl)ethylene according to claim 1 comprising:

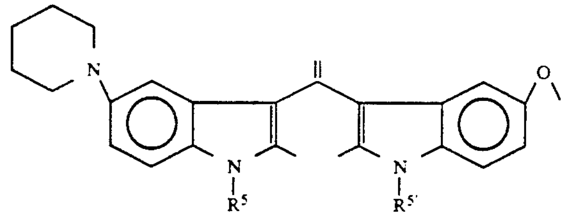

3. A bis-(indolyl)ethylene according to claim 1 comprising:

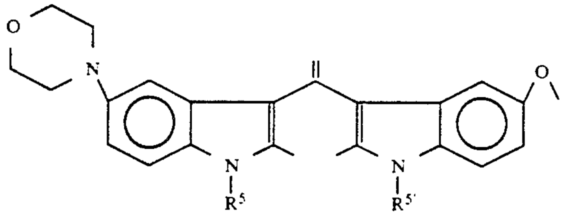

4. A bis-(indolyl)ethylene according to claim 1 comprising:

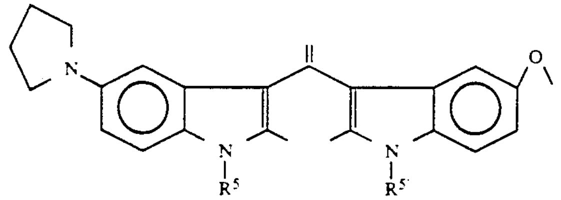

5. A bis-(indolyl)ethylene according to claim 1 comprising:

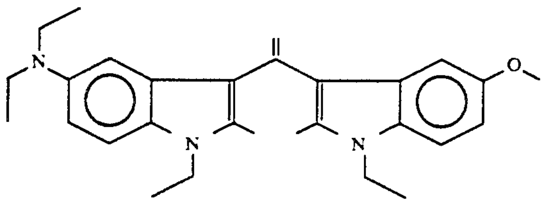

6. A bis-(indolyl)ethylene according to claim 1 comprising:

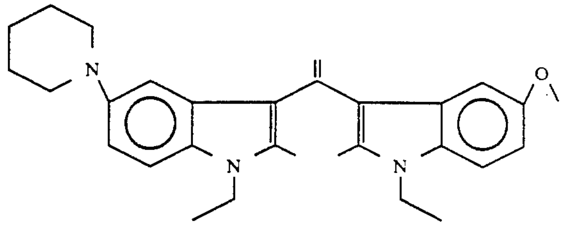

7. A bis-(indolyl)ethylene according to claim 1 comprising:

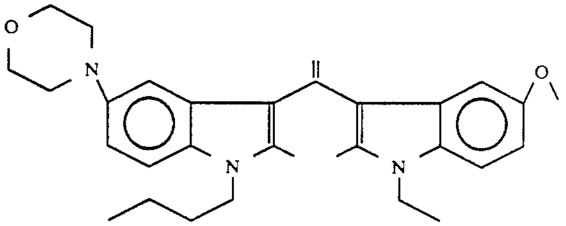

8. A bis-(indolyl)ethylene according to claim 1 comprising:

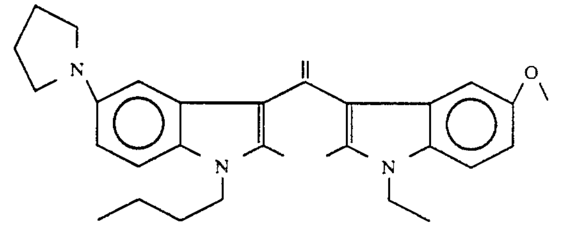

9. A Chromogenic bis-(indolyl)ethylenes of the formula

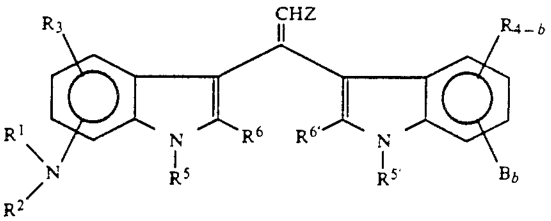

wherein $R^1$ and $R^2$ are selected from the group consisting of alkyl ($C_1$-$C_8$), cycloalkyl ($C_3$-$C_6$), phenyl, and phenyl substituted by alkyl ($C_1$-$C_8$) or alkoxy ($C_1$-$C_8$), wherein R, B, b, $R^5$, $R^{5'}$, $R^6$, $R^{6'}$ and Z are as previously defined in claim 1.

10. A bis-(indolyl)ethylene according to claim 9 comprising:

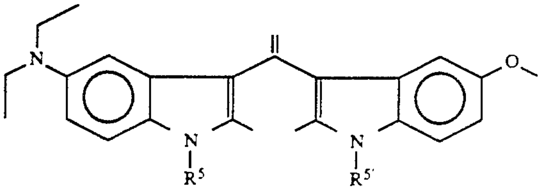

* * * * *